(12) United States Patent
Wieder (10) Patent No.: US 11,547,327 B2
(45) Date of Patent: Jan. 10, 2023

(54) ANALYTE MEASUREMENT SYSTEM AND INITIALIZATION METHOD

(71) Applicant: Roche Diabetes Care, Inc., Indianapolis, IN (US)

(72) Inventor: Herbert Wieder, Lampertheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 398 days.

(21) Appl. No.: 16/094,510

(22) PCT Filed: May 8, 2017

(86) PCT No.: PCT/EP2017/060898
§ 371 (c)(1),
(2) Date: Oct. 18, 2018

(87) PCT Pub. No.: WO2017/194458
PCT Pub. Date: Nov. 16, 2017

(65) Prior Publication Data
US 2019/0117135 A1    Apr. 25, 2019

(30) Foreign Application Priority Data

May 13, 2016  (EP) ..................................... 16169640

(51) Int. Cl.
*A61B 5/145*    (2006.01)
*A61B 5/1486*   (2006.01)
(Continued)

(52) U.S. Cl.
CPC ........ *A61B 5/14532* (2013.01); *A61B 5/1495* (2013.01); *A61B 5/14865* (2013.01); *A61B 5/7495* (2013.01); *A61B 2562/085* (2013.01)

(58) Field of Classification Search
CPC .............. A61B 5/14532; A61B 5/7495; A61B 5/14865; A61B 5/1495; A61B 2562/085;
(Continued)

(56) References Cited

U.S. PATENT DOCUMENTS 8,060,173 B2   11/2011  Goode, Jr. et al.
8,229,534 B2    7/2012  Brister
(Continued)

FOREIGN PATENT DOCUMENTS

CN          101091114       12/2007
RU          2013116993      10/2014
WO      WO 2015/100109 A     7/2015

OTHER PUBLICATIONS

Office action in related CN201780029181.2 dated Sep. 28, 2020.

*Primary Examiner* — Devin B Henson
*Assistant Examiner* — Justin Xu
(74) *Attorney, Agent, or Firm* — Woodard, Emhardt, Henry, Reeves & Wagner, LLP (57) ABSTRACT

Disclosed is a method for initializing an analyte measurement system (1, 2, 3), the analyte measurement system (1, 2, 3) being designed for continuous in-vivo measurement of a body fluid analyte concentration. The method including the steps of:
a) providing the analyte measurement system (1, 2, 3,) with a control device (3) and a separate skin-mountable patch device (1, 2), the patch device (1, 2) including a disposable unit (1) and an electronics unit (2), the disposable unit (1) including a transcutaneous analyte sensor (10) and machine-readable sensor identifier (121), the electronics unit (2) being configured to releasable couple for an application time period to the disposable unit (1);
b) providing a number of stored initialization data sets in a remote database system (4), each stored initialization data set comprising initialization data for an analyte sensor batch;

(Continued)

c) reading, via a reading device (31) of the control device (3), the sensor identifier from the disposable unit (1) into the control device (3) and transmitting the sensor identifier to the remote database system;

d) determining a matching initialization data set, the matching initialization data set being a stored initialization data set that matches the sensor identifier;

e) transmitting the matching initialization data set from the remote database system to the control device (3);

f) transmitting the matching initialization data set to the electronics unit (2) and storing the matching initialization data set in a memory (21) of the electronics unit (2).

12 Claims, 3 Drawing Sheets

(51) Int. Cl.
*A61B 5/1495* (2006.01)
*A61B 5/00* (2006.01)

(58) Field of Classification Search
CPC ............ A61B 5/14535; A61B 5/14539; A61B 5/14542; A61B 5/14546; A61B 5/6833; A61B 2562/08; A61B 2560/0223; A61B 2560/0228; A61B 2560/0238
See application file for complete search history.

(56) References Cited

U.S. PATENT DOCUMENTS

| | | |
|---|---|---|
| 9,476,088 B2 | 10/2016 | Craggs et al. |
| 2004/0231772 A1* | 11/2004 | Leonard ............. A61B 1/00062 150/161 |
| 2007/0038044 A1* | 2/2007 | Dobbies ............. A61B 5/14517 600/316 |
| 2008/0183388 A1 | 7/2008 | Goodrich |
| 2008/0278333 A1* | 11/2008 | Fennell ............. A61B 5/14532 340/573.1 |
| 2010/0222648 A1* | 9/2010 | Tan ........................ G16H 40/40 600/301 |
| 2010/0240079 A1* | 9/2010 | Jackson ........... A61B 5/150022 435/14 |
| 2010/0270180 A1* | 10/2010 | Liu ..................... A61B 5/14865 205/794.5 |
| 2013/0245401 A1* | 9/2013 | Estes ..................... A61B 5/7203 600/309 |
| 2014/0278189 A1 | 9/2014 | Vanslyke |
| 2015/0002270 A1* | 1/2015 | Otis ..................... A61B 5/6821 340/10.1 |
| 2015/0073241 A1* | 3/2015 | Lamego ............... A61B 5/1459 600/326 |
| 2015/0087942 A1* | 3/2015 | Brauker ............. A61B 5/15142 600/347 |
| 2015/0112264 A1* | 4/2015 | Kamen ................. G16H 40/67 604/151 |
| 2015/0207796 A1* | 7/2015 | Love ..................... H04W 12/06 600/345 |

* cited by examiner

ANALYTE MEASUREMENT SYSTEM AND INITIALIZATION METHOD

FIELD OF DISCLOSURE

The present disclosure lies in the field of analyte measurement, in particular glucose measurement, in a body fluid or body tissue. It particular relates to the design of analyte measurement system and the initialization of such systems.

BACKGROUND

Continuous analyte measurement systems are known for the invasive and in-vitro measurement of an analyte concentration in a patient's body fluid or tissue. They are used, for example, for the continuously monitoring a diabetic's glucose level over an extended time period for a number of days up to several weeks after which they are replaced, typically directly by the patient, a relative, or the like (commonly referred to as "user").

The sensors that are used in such system are typically based on an amperometric measurement principle and include a number of electrodes that are arranged on a typically elongated electrode carrier. For the application, an electrode-carrying portion of the electrode carrier is placed in the patient's subcutaneous tissue and the glucose concentration is measured in the interstitial fluid. A variety of sensor and electrode designs is known in the art. The sensor electrodes and the surrounding analyte-comprising body fluid and/or tissue, in combination, form an electrochemical cell. Where not explicitly stated differently, such arrangement is also assumed in the following.

SUMMARY OF DISCLOSURE

Since the sensors respectively patch devices that are attached to the skin and include the sensor as such are generally exchanged by users of no or limited corresponding training and experience, and since further no medical or clinical environment is generally available, it is highly desirable that all involved steps are as simple and fault-proof as possible. Due to health cost constraints, the overall costs (largely determined by the disposable costs) should be low.

An aspect of major importance in the context of analyte measuring systems is the calibration, or more generally, initialization that is typically required for each individual sensor.

In a known approach, required initialization data, in particular calibration data, are directly stored into and provided as integral part of each disposable, which, however, is comparatively complex from a manufacturing point of view.

In another known approach, some data storage, such as a pre-programmed memory device (e. g. Read Only Memory, ROM), is provided with each sensor or package of sensors. The data storage may be provided in form of a tab, key, or the like, which is mated with the sensor respectively patch device and stores the corresponding initialization data. This approach, however, requires the additional manufacture, programming and supply of the memory device, and—typically even more critical—requires the patch device to comprise a corresponding electrical and/or mechanical interface.

The WO 2013/020045 A2 discloses arrangements for the remote calibration of medical devices and relates to laboratory-based devices. For example, a computing device may receive a calibration request over a network from a test device. The calibration request may include at least one identifier. The computing device may determine, based at least in part on the identifier, calibration information corresponding to a substance for use with the test device. The computing device may send to the test device the calibration information corresponding to the substance. In some instances, the identifier received from the test device may identify a particular batch of reagent as the substance, and the calibration information may be batch-specific calibration information that corresponds to the particular batch of reagent.

The US 2014/0012117 A1 discloses a Continuous Glucose Measurement (CGM) device that includes a sensor system identifier affixed on a housing of the CGM device. The sensor system identifier is used to generate a device ID, to establish a channel and to generate a sensor security code used for additional security in the glucose monitoring system. With regard to other information that may be captured by the image capture module, one or more codes may be provided, whereby the CGM module can derive sensor information, for example sensor expiration, sensor lot information, sensor calibration information, etc. The CGM module may initiate a request for a code, in response to which the user may capture an image of the code, after which the CGM module reads and interprets the code to obtain information useful for the function and/or control of the sensor and/or display and processing of the sensor data.

The US 2012/0283542 A1 discloses methods for calibrating analyte measuring devices. Here, a calibration measurement of the first phase is performed at the time of the analyte sensor being manufactured. Typically, representative sensors from a large batch or lot of analyte sensors are tested at the site of manufacture, and a calibration code is assigned to the sensor lot. The calibration code may then be used in association with the analyte-measuring device to convert the raw analyte signal into an analyte concentration. A manufacturer or user of the device may enter the code into the device, or a data processor of the device, for such data conversion.

The U.S. Pat. No. 9,011,332 B2 discloses devices and methods for the in vivo monitoring of an analyte. Calibration data is simply factory-determined calibration measurements which can be inputted into an on-skin sensor control unit using a receiver or may alternatively be stored in a calibration data storage unit within the on-skin sensor control unit itself. The calibration data storage unit may be a readable or readable/writeable memory circuit.

The WO 2006/122741 A1 discloses a handheld BG meter that receives batch specific information via a network.

It is an overall objective to improve the state of the art regarding the initialization of an analyte measurement system. In particular, it is an objective to provide a system that is generally cost-efficient in manufacture and simple and fault-proof during application by a user. In a general way, the overall objective is achieved by the subject of the independent claims. Exemplary or particularly favourable embodiments are defined by the dependent claims and the overall disclosure.

In an aspect, the overall objective is archived by a method for initializing an analyte measurement system. The analyte measurement system is designed for continuous in-vivo measurement of a body fluid analyte concentration. The method includes the step of: (a) providing the analyte measurement system with a control device and a separate skin-mountable patch device, the patch device including a disposable unit and electronics unit, the disposable unit including a transcutaneous analyte sensor and machine-readable sensor identifier. The electronics unit is configured to releasable couple for an application time period to the disposable unit. The method further includes the step of (b) providing a number of stored initialization data sets in a remote database system, each stored initialization data set comprising initialization data for an analyte sensor batch. The method further includes the step of (c) reading, via a reading device of the control device, the sensor identifier from the disposable unit into the control device and transmitting the sensor identifier to the remote database system. Reading the sensor identifier into the control device is equivalent with transmitting the sensor identifier from the disposable unit to the control device. The method further includes the step of (d) determining a matching initialization data set, the matching initialization data set being a stored initialization data set that matches the sensor identifier. The method further includes the step of (e) transmitting the matching initialization data set from the remote database system to the control device. The method further includes the step of (f) transmitting the matching initialization data set to the electronics unit and storing the matching initialization data set in a memory of the electronics unit.

According to the method, the initialization data that are required for initializing the analyte sensor at respectively before the beginning of its use period are stored in a remote data base and are transferred from the remote database to the electronics unit of the patch device at respectively before the start of the application time period. In this way, the need for manually inputting or transmitting initialization data or for inserting a data storage device, such as a ROM (Read Only Memory) key which stores the initialization data, is avoided. The memory of the electronics unit is a writable memory and generally stores the initialization data only temporarily, i. e., for the application time period of a specific analyte sensor. When replacing the analyte sensor with a new sensor, the data may be replaced by the matching initialization data set of the new sensor.

Typically, a remote data base is provided and hosted by a provider or manufacturer of the analyte measurement system and provided by way of corresponding computing infrastructure, such as servers, running a corresponding software, in particular a database software.

The phrase "remote database system" refers, in combination, to the remote database as such, corresponding database software, as well as the hosting computing infrastructure.

Each initialization data set that is stored by the remote database corresponds to a single or a number of sensor batches for which the corresponding initialization data match. Each sensor batch consists of a plurality of sensors with substantially identical characteristics, such that all of them can be used with the same initialization data set.

For carrying out the step of determining a matching initialization data set, the remote database may store a matching correspondence between sensor identifiers on the one hand and initialization data sets on the other hand. The matching correspondence may be stored, e. g., by way of a table, such as a look-up table, or by way of a matching formula which defines the matching relation between sensor identifiers on the one hand and initialization data sets on the other hand. In a further variant, the sensor identifier includes a batch identifier as part thereof.

Generally, the initialization data may include any data that are required for the use of a specific sensor respectively disposable unit and need, at least partly, be available on the patch device that is attached to the skin.

In an embodiment, the initialization data sets each include at least one of a batch identifier, sensor calibration information, and a sensor expiry date. In an embodiment, the method includes the step of calibrating the analyte sensor using the matching initialization data. For this purpose, the electronics unit may be configured to apply a calibration routine on the signals that are provided by the analyte sensor, with parameters of the calibration routine being or being computed from the calibration information. "Calibration data" or "calibration information" may include any data that are required to convert raw electrical sensor signals, such as measured electrode currents and/or voltages, into the actual analyte concentration data, e. g. glucose concentration data.

In the following, it is assumed that all initialization data that are retrieved from the remote database are transmitted to the electronics unit as part of the patch device.

In an embodiment, the sensor identifier is unique for the analyte sensor. For this type of embodiment, the sensor identifier is a unique serial number that distinguishes the sensor from all other sensors. The identifier may be or include a running number, but may also include further information, such as a production period, production date and/or a batch identifier.

In an embodiment, the sensor identifier is provided on a package of the disposable unit and/or on an insertion device in releasable mechanical coupling with the analyte sensor.

During application, the skin-mounted disposable components that are, in addition to the electronics unit, carried directly at the body, namely the analyte sensor with a corresponding adhesive pad, as well as the required mechanical and electrical coupling or interface structure for coupling with the electronics unit, shall generally be as discrete and slim as possible and further have a footprint as small as possible. In dependence of the specific design, it may therefore not be possible to provide the sensor identifier as part of these skin-mounted components. In typical embodiments, however, each disposable unit is provided with an insertion device for transcutaneous placement of the analyte sensor in the patient's tissue. Such insertion device may comprise a handle and a guide for manual guided insertion of the analyte sensor, and/or be an e. g. spring-driven automated inserter. A variety of insertion devices is known in the art. Typically, the insertion device is provided in an application-ready state in coupling with the analyte sensor. After insertion of the analyte sensor into the tissue, the insertion device is removed and discarded. Since the insertion device is not carried on the body during the application time, the requirements regarding size and shape are less strict. The insertion device may accordingly carry the sensor identifier, e. g. in form of a tag, label, or imprint.

In a further embodiment, the sensor identifier is provided on the outside of a package of the disposable unit. The package on which the sensor identifier is provided may be an individual primary package, in particular a sterile package, of each individual sensor. Alternatively or additionally, it may be provided on a secondary package for a set of a number of, e. g. four sensors. The sensor identifier may be provided on a package in addition to the insertion device for redundancy purposes. Providing the sensor identifier on a package is further favorable in embodiments where no individual insertion device is provided with each disposable unit, but a multi-use insertion device is used instead with a number of disposable units respectively sensors in sequence.

In some embodiments that are discussed in more detail further below, sensor identifiers are read from a number of disposable units/sensor into the control device in sequence, well before their actual use. In such embodiments, it may also be favorable to provide the sensor identifier on a package since access, in particular optical access, to the insertion device inside the sterile package may be limited or not given at all. Alternatively or additionally, however, the primary (sterile) package may be at least partly transparent and the disposable unit with the insertion device may be positioned inside the primary package such that the sensor identifier is (optically) accessible. In a further variant, the sensor identifiers are provided separately, e. g. on an information leaflet that is provided with each disposable unit or a number of disposable units.

Generally, the step of reading the sensor identifier into the reading device may be carried out before placing the sensor into the tissue. Where the sensor identifier is subsequently detached and removed from the analyte sensor, e. g. as part of an insertion device as mentioned before, the sensor identifier may alternatively be red into the control device after its removal.

In an embodiment, the sensor identifier is provided as optically readable code and the reading device of the control device is an optical reading device, in particular a camera. In a typical embodiment, the optically readable code is a 2D-barcode, e. g. a Data Matrix as known in the art, but may also be or include another type of optically readable code, such as another type of 2D-barcode, a 1-D-barcode, or a machine-readable (alpha-)numeric code. The reading device typically is a—for example general purpose—camera device, but may also be other optical reading device, such as a dedicated bar code scanner. In embodiments where the sensor identifier is provided in coded form, for, e. g. as bar code, the control device is further configured to decode the coded identifier and the method includes a corresponding decoding step.

For transmitting the sensor identifier to the remote data base system and transmitting the matching initialization data set from the remote data base to the control device, the method includes establishing a database communication link between the control device and the remote database system. Likewise, the method includes the step of establishing a local communication link between the control device and the electronics unit.

In an embodiment, the method includes transmitting the sensor identifier to the remote database in step (c) and transmitting the matching initialization data set from the remote database to the control device in step (e) via a web-based database communication link.

In an embodiment, the method includes the step of: (c1) altering sensor status information in the remote data base system, the sensor status information corresponding to the sensor identifier, with step (c1) being carried out after step (c) as explained before. This type of embodiment enables the database system to record the use of a particular analyte sensor and in particular to prevent the double-use of a sensor. As explained before, the sensor identifier is in favorable embodiments unique for each analyte sensor. Furthermore, each analyte sensor is used for a limited application time period and is subsequently discarded. Consequently, for each individual analyte sensor, there is only one point in time where the initialization information should be transmitted from the remote database system to the control device, and respectively, the electronics unit, while any further request for transmittal of the initialization information may be indicative of a handling error or a misuse.

In an embodiment, the remote database system stores the identifiers of all available analyte sensors, e. g. all analyte sensors that have been produced respective delivered. Here, the sensor status information may, in a basic embodiment, be a status bit that is swapped after transmittal of the sensor identifier to the remote database system, thus changing the corresponding sensor status information from "non-activated" to "activated". In a variant, the remote database system does not store all available sensor identifiers right away, but the sensor identifier is, after receiving by the remote database system, added to a list of activated analyte sensors.

The method may further include, after transmitting the sensor identifier to the remote database system in step (c), carrying out a step (c') of checking the sensor status information and carrying out subsequent steps only if the sensor status information indicates that the corresponding analyte sensor has not been activated before. If checking the status information indicates that the analyte sensor has been used before, a corresponding message is favorably transmitted from the remote data base system to the control device and a corresponding message is displayed to the user.

In an embodiment, step (c) includes reading the sensor identifier from each of a number of disposable units into the control device in a sequence, and transmitting the sensor identifiers to the remote database system in common. Step (d) includes determining a matching initialization data set for each of the sensor identifiers. Step (e) includes transmitting the matching initialization data sets corresponding to each sensor identifier from the remote database system to the control device in common. A method according this type of embodiment further includes the steps of (e1) reading, via the reading device, the sensor identifier from a specific disposable unit from the number of disposable units into the control device a second time. The method further includes the step of (e2) determining a specific matching initialization data set from the matching initialization data sets, the specific matching initialization data set matching the sensor identifier of the specific disposable unit. For this type of embodiment, step (f) further includes transmitting the specific matching initialization data set to the electronics unit and storing the specific matching initialization data set in the memory of the electronics unit.

When requesting the initialization information from the remote database system only directly prior to activating a new analyte sensor, problems may in principle occur in situations where, e. g., the for example web-based remote database communication link cannot be established for any reason or the remote database system is temporary non-operative.

For this type of embodiment, the steps that involve a data communication between the control device and the remote database system, in particular transmitting sensor identifiers to the remote database system and receiving initialization data sets from the remote database system, as well as the preparatory step of reading sensor identifiers into the control device, are carried out in common for a number of disposable units and may be carried out some time prior to the usage. Typically, the number of disposable units belong to one or more packages of disposable units. A user may request the calibration information for all of the disposable units of a package e. g. directly after purchase. In case the steps are carried out at a point in time prior to the time when a first of the number of sensors shall actually put into operation, the procedure may further be repeated at a later point in time in case it cannot be successfully completed e. g. due to database communication problems.

A method according to this type of embodiment further includes storing the matching initialization data sets corresponding to each sensor identifier after receiving them from the remote database system in a memory of the control device until a specifically disposable unit is actually put into operation and the corresponding initialization data set is actually used. The matching initialization data sets corresponding to the number of disposable units are accordingly temporarily stored by the control device in a (small) local database.

It is to be noted that for this type of embodiment the sensor identification code is red into the control device twice: a first time prior to requesting the initialization data sets from the remote database system, and a second time when actually putting a specific sensor unit into use. Due to the local database in the controller, however, the steps for putting a specific sensor into use can be carried out locally and without relying on the remote database link.

For this type of embodiment, the sensor identifier is further provided in a way that allows reading it with the reading device prior to opening a sterile package in which each disposable unit is typically individually provided. Therefore, the sensor identifier may be provided on the outside of the sterile package in addition and/or or alternatively to e. g. an insertion device, if accessing the sensor identifier is not possible otherwise.

In an embodiment, step (f) includes transmitting the sensor identifier to the electronics unit and storing the sensor identifier in the memory of the electronics unit. This type of embodiment is particularly favorable in the context of complaint analysis. In embodiments with a number of disposable units as explained before, the steps particularly relate to the specific sensor identifier.

In an embodiment, the remote database stores, for each analyte sensor batch, analyte sensor sub-batch and/or disposable unit validity information. The validity information indicates whether a batch, sub-batch or disposable unit is fine for use. For this type of embodiment, the method includes evaluating the validity information in step (d). For this type of embodiment, the method further includes transmitting an invalidity indicator from the remote database to the control device in addition or alternatively to the matching initialization data set in step (e) in case the validity information indicate that the batch, sub-batch or disposable unit is not fine for use. The method may further include the control device providing a warning message upon receiving invalidity indicator in step (f). Optionally, the steps of transmitting the matching initialization data set to the electronics unit and storing the matching initialization data set in a memory of the electronics unit may not be carried out in this case.

In case, e. g. a manufacture problem or the like is identified for individual batches or sub-batches, the corresponding validity information may be changed, indicating that a disposable of the affected batch or sub-batch should not be used and an invalidity indicator is transmitted as explained before. In a variant, validity information is transmitted in any case, the validity indicator indicating whether or not the batch, sub-batch or disposable unit is fine for use. For such embodiments, the validity information may not be evaluated in step (d) by the remote database, but by the control device after transmittal to the control device.

That is, decision whether or not a specific disposable unit is fine for use is made in the control device. In a further variant, the remote database stores an invalidity indicator instead of initialization data for a batch, sub-batch or disposable unit if it is not fine for use. For this type of embodiment, the method includes replacing the initialization data with an invalidity indicator if a batch, sub batch or disposable unit is not fine for use.

In a further aspect, the overall objective is achieved by a method for providing complaint analysis data for an analyte sensor of an analyte measurement system that is designed for continuous in-vivo measurement of a body fluid analyte concentration. The method includes the step of (I) carrying out a method for initializing the analyte measurement system as discussed before, wherein the method for initializing the analyte measurement system includes transmitting the sensor identifier to the electronics unit and storing the sensor identifier in the memory of the electronics unit. The method further includes the step of (II) transmitting the sensor identifier from the memory to an analysis device. The method further includes the step of (III) determining matching production related data by matching the sensor identifier with a plurality of production related data sets that are stored in a production system data base, the matching production related data matching the sensor identifier. The step of determining matching production related data may be carried out by the analysis device.

In some occasions, it is desirable to carry out an analysis of an analyte sensor as described before that has already been used by a patient. This is the case, e. g. for a failure analysis of a potentially defective sensor and/or in case of a medical incident, such as a severe hyperglycemia or hypoglycemia of a person with diabetes using a continuous glucose monitoring system. According to the state of the art, however, an already used disposable unit and in particular analyte sensor cannot be easily returned to the manufacturer or the like and analyzed for a number of reasons. In particular, an analyte sensor that had already been placed in the tissue may be contaminated. Furthermore, in order to return the typically electrochemical/amperometric analyte sensor from the patient in an operative state that allows a meaningful analysis, it would need to be stored and shipped in a buffered solution, which is generally unfeasible.

A variety of production-related data that is highly valuable for the complaint analysis, however, is generally available in a production database and/or a database of a production management system. Such production-related data may include one or more of: time and/or date of production; batch identifier of used raw materials; environmental conditions during production; potential sub-batch of the analyte sensor; order of process steps during manufacture; print image of sensor electrodes during e. g. screen-printing of the sensor electrodes, and the like.

In addition to the complaint analysis for a specific analyte sensor respectively disposable unit, matching individual sensor identifiers with production-related data as available for this type of embodiment is particularly useful for identifying systematic problems that may be associated, e. g., with a particular batch of raw materials or particular environmental conditions and may be identified manually and/or automatically using available statistical methods such as correlation analysis.

In a further aspect, the overall objective is achieved by a skin-mountable patch device for use in an analyte measurement system, the analyte measurement system being designed for continuous in-vivo measurement of a body fluid analyte concentration. The patch device includes a disposable unit and an electronics unit. The disposable unit further includes a transcutaneous analyte sensor and a machine-readable sensor identifier. The electronics unit is configured to releasable couple for an application time period to the disposable unit. The electronics unit is further configured to receive a matching initialization data set from a separate control device and to store the received matching initialization data set in a memory of the electronics unit. In an embodiment, the analyte is glucose.

The disposable unit typically includes an adhesive pad with an adhesive side for attachment to a patient's skin. The analyte sensor is a typically electrochemical sensor that includes a number of electrodes and operates according to an amperometric measurement principle as generally known in the art. The electrodes are typically arranged on an elongated electrode carrier that is attached to an adhesive pad and projects from the adhesive side of the adhesive pad. Typically, the electrode carrier is realized as elongated piece of substrate. In case of the electrode carrier being semi-rigid or soft (not sufficiently stiff or rigid to allowing direct tissue insertion), a rigid auxiliary insertion element, e. g. in form of a cannula inside which the sensor is placed for the insertion, may be present. After successful insertion, the auxiliary insertion element is retracted out of the tissue.

In addition to the elements that remain attached to the body for the application time period and form a sensor part of the disposable unit, the disposable unit may include an insertion device as explained before in order to ensure a guided an optionally automated insertion process. Optionally, such insertion device may be designed for e. g. automated retraction of the auxiliary insertion element and may form a common unit with the insertion element. The design of suited sensors an insertion devices is generally known in the art. The insertion device may be provided with the sensor part as readily assembled and compact unit. After insertion of the analyte sensor into the tissue and optionally retracting the auxiliary insertion element, the insertion device is decoupled from the sensor part and discarded. As explained before, the insertion device may carry the sensor identifier.

For releasable electrical and mechanical coupling between the disposable unit, in particular the sensor part of the disposable unit, and the electronics unit, an interface structure, such as a snap-fit or catch-lock structure is provided on the sensor part and the electronics unit.

For the data exchange with the control device, the electronics unit includes a wireless electronics communication unit that is designed to exchange data with the control device e. g. according to the Bluetooth standard or any other suited general purpose or proprietary communication standard and/or protocol via a local communication link as explained before. Data that are transmitted from the control device to the electronics unit particularly include the initialization data set. Via the electronics communication unit, analyte concentration data or data correlated with analyte concentration are further transmitted from the electronics unit to the control device.

In dependence of the overall system architecture, the electronics unit may further include amperometric measurement circuitry, such as a potentiostat circuit, signal condition circuitry, such as filters, or amplifiers, and the like. In alternative embodiments, however, the measurement circuitry is arranged in a structurally distinct further disposable electronics unit that may be integral with the sensor part of the disposable unit. In such a design, the electronics unit and the disposable electronics unit are designed for releasable operative coupling and signal or data exchange.

Further in dependence of the overall system architecture, a power supply, e. g. in form of a battery, may be present in the electronics unit and/or the optional disposable electronics unit.

During application, the patch device with the electronics unit and the disposable unit, in particular the sensor part of the electronics unit, form a common compact arrangement.

The electronics unit, however, is designed for a substantially longer lifetime as compared to the disposable unit. Typically, the electronics unit has a lifetime or application time in the range of a year or more and is typically used with a plurality of disposable units in sequence. The disposable unit, in contrast, is designed for a single application time period in a range of, e. g., one week up to three weeks.

Further aspects and particular embodiments of the patch device are discussed above in the context of methods in accordance with the present disclosure as well as further below in the context of exemplary embodiments.

In a further aspect, the overall objective is achieved by an analyte measurement system. The analyte measurement system includes a skin-mountable patch device as explained before, and a control device. The control device includes a reading device. The control device is configured: to read, via the reading device, the sensor identifier from the disposable unit into the control device and to transmit the sensor identifier to the remote database via a database communication link. The control device is further configured to receive a matching initialization data set from the remote database via the database communication link. The control device is further configured to transmit the matching initialization data set to the electronics unit via a local communication link and to store the matching initialization data set in a memory of the electronics unit. The analyte measurement system may further include a remote database system.

The control device is designed for controlling operation of the analyte measurement system and is in communication with the electronics unit via the local communication link as explained before.

The control device is typically microcomputer and/or microcontroller based and is designed to provide analyte measurement results, e. g. glucose measurement results, to the user. The control device is further typically designed for storing measured blood glucose data and optionally performing statistical analysis, such as trend analysis, and the like.

In a typical embodiment, the control device is a general-purpose portable device, in particular a smartphone with a corresponding control code.

Using a smartphone as control device is particularly favorable since it is carried respectively accessible by many people substantially continuously. A smartphone further readily provides all hardware components or modules that are required for the control device. In particular, the typically present camera of a smartphone may serve as reading device for reading and decoding data identifiers as explained before.

Further, a smartphone typically includes a Bluetooth communication module that may favorably serve as local control device communication unit for establishing the local communication link with the electronics communication unit of the electronics unit as explained before.

In an embodiment, the database communication link includes at least one of a WLAN communication link, and a general purpose mobile device communication link, in particular a web-based communication link. A general purpose mobile communication link may in particular be established via general mobile cellular device communication infrastructure, e. g. according to the 3G standard and/or the UMTS standard and/or the GSM standard. The database communication link may especially be a Web- and/or internet based communication link.

Further aspects and particular embodiments of the control device are discussed above in the context of methods in accordance with the present disclosure as well as further below in the context of exemplary embodiments.

Embodiments of a patch device and an analyte measurement system in accordance with the present disclosure may in particular be designed to carry out a corresponding embodiment of an initialization method and/or a method for providing complaint analysis data. Likewise, methods in accordance with the present disclosure may in particular be carried out with corresponding embodiments of an analyte measurement system and/or patch devices. Therefore. The disclosure of particular embodiments of an initialization method and/or a method for providing complaint analysis data disclose the same time corresponding embodiments of an analyte measurement system respectively a patch device that is adapted to carry out such method embodiment. Likewise, the disclosure of particular embodiments of an analyte measurement system respectively a patch device disclose at the same time an embodiment of an initialization method and/or a method for providing complaint analysis data that is carried out.

EXEMPLARY EMBODIMENTS

Figure 1:
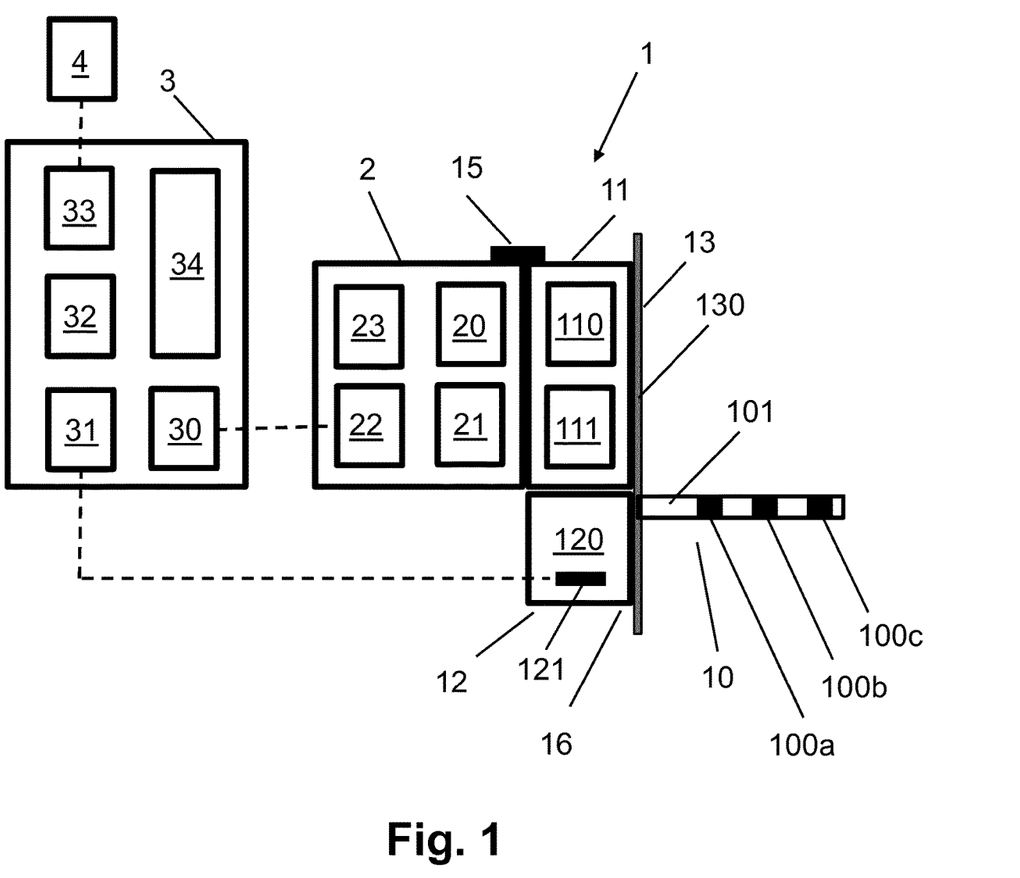
FIG. 1 shows an exemplary embodiment of an analyte measurement system.

In the following, reference is first made to FIG. 1. FIG. 1 shows an exemplary arrangement of a continuous glucose measurement system in accordance with the present disclosure in a schematic functional view. The continuous glucose measurement system includes a patch device with a disposable unit 1 and an electronics 2, and a control device 3. FIG. 1 further shows a remote database 4 which, as such, is not part of the measurement system.

The specific arrangement and relative locations of the individual elements, modules, components or units does not imply any particular design and/or geometric arrangement, unless explicitly stated differently. By way of example, the analyte is glucose and the analyte measurement system designed for measuring glucose concentration inside the interstitial tissue. Alternatively, the measurement system may be design for measurement of another analyte.

The disposable unit 1 includes a senor 10, a disposable electronics unit 11, an insertion device 12, and an adhesive pad 13.

The sensor 10 includes an electrode carrier 101 that is designed for transcutaneous placement in a patient's tissue using the insertion device 12. In its subcutaneous portion, i. e. its portion that is arranged under the skin during application, the electrode carrier 101 carries an exemplary number of three electrodes 100a, 100b, 100c, the three electrodes being a working electrode, a reference electrode, and a counter electrode. Other sensor arrangements with another number of electrodes may be used as well. Suited sensor designs that may be used in the context of analyte measuring patch 1 are known in the art.

The adhesive pad 13 comprises an adhesive surface 130 that is designed to be attached to the patient's skin, with the sensor 10 respectively the electrode carrier 101 projecting from the adhesive surface 130 perpendicularly (as exemplarily shown) or in another desired angle. The three electrodes 100a, 100b, 100c are in galvanic or wired connection (not shown) with the disposable electronics unit 11 that is permanently arranged on and attached to the non-adhesive side of the adhesive pad 13, pointing away from the skin. In the shown embodiment, the sensor 10, the adhesive pad 13 and the disposable electronics unit 11 form a non-separable disposable unit that is designed to be used for a limited time of a number of days of up to a number of weeks and to be subsequently discarded.

The disposable electronics unit 11 exemplarily includes a power supply 110 in form of a battery and disposable circuitry 111. The power supply 110 powers, in operation, generally both the disposable circuitry 111 and the electronics unit 2. The lifetime of the battery fits and is favourably somewhat longer than the intended application time of, e. g., a number of weeks.

The disposable electronics unit 11 includes the measurement circuitry such as, e. g., filters, signal amplifiers, coupling amplifiers, and potentiostat circuitry, in accordance with the design of the sensor 10.

The electronics unit 2 is designed for a substantially longer life and application time as compared to the disposable unit 1, of e. g., one year. An interface structure 15 is present between the disposable unit 1, exemplary the disposable electronics unit 11, and the electronics unit 2 for releasable mechanical and electrical coupling. The interface structure 15 includes mating electric contacts as well as a mechanical interface structure wit, e. g. snap-fitting elements, catches, latches, or the like as generally known in the art.

The electronics unit 2 exemplarily includes a backup battery 20, a memory 21, an electronics communication unit 22 and general electronics unit circuitry 23.

In the shown exemplary setup, the backup battery 20 backups the memory 21 and may optionally generally power the electronics unit 2 when it is temporarily not connected to a disposable electronics unit 11, e. g. during sensor replacement.

The electronics communication unit 22 is designed for communicating and exchanging data with a local control device communication unit 30, exemplarily via Bluetooth. The electronics unit 2 is, like the disposable electronics unit 11, favourably enclosed by a casing. In an assembled state, the overall arrangement is, including the electrical coupling, favourably water tight or a water protected, allowing, e. g. bathing, showering, and the like.

The insertion device 12 is designed for manual or automated, e. g. spring driven, insertion and includes an inserter arrangement 120 (not shown in detail) as generally known in the art. The sensor identifier is provided in machine-readable form, exemplary as Data Matrix 121, on a housing of the inserter device 121. The sensor identifier is unique and may be provided, e. g., on an adhesive tag, ink-printed directly onto the housing of the inserter device, laser-engraved, or the like. Alternatively or additionally, the Data Matrix 121 or another sensor identifier may be provided on a e. g. primary (sterile) package, a secondary package, an information leaflet, or the like, or a separate carrier, such as piece of paper or card board.

The disposable unit 1 is favourably provided readily assembled with the inserter device 12 being in place. After carrying out the insertion movement as explained before, the insertion device 12 is removed and discarded.

In this example, the insertion device is connected to the adhesive pad via a dedicated releasable inserter interface structure 16, independent from the before-mentioned coupling structure 15. The Data Matrix 121 is favourably arranged such that it is readable with the inserter device 12 being connected to the adhesive pad 13. Typically, the sensor identifier is read into the control device 3 as explained further below prior to inserting the sensor 10, e. g. directly after removing the disposable unit from its sterile package, which, however, is not essential. In an alternative embodiment, the insertion device 12 and the electronics unit 2 are designed to alternatively couple to the disposable electronics unit 11 via the coupling structure 15. In such embodiments, the insertion process is first carried out, using the insertion device 12. After removal of the insertion device 12, the electronics unit 2 is coupled via the coupling structure 15.

In a further variant, the (backup-) battery 20 is not present in the electronics unit 2. In a still further variant, the battery 110 is not present, but the disposable circuitry 111 is powered via the battery 20 which, in this case, is not a backup battery, but the main power supply and is designed for a lifetime that corresponds to the electronics unit 2 of, e. g.

several months, a year, or longer, and/or may be rechargeable and/or replaceable. In such embodiments where only data are transmitted between the disposable electronics unit 11 and the electronics unit 2, no galvanic interface may be provided, but the communication may be via wireless data communication units, e. g. via Near Field Communication (NFC) that may be part of the disposable circuitry 111 and the general electronics unit circuitry 23, respectively.

In still further embodiments, the disposable electronics unit 11 is not present but the functionality of the disposable circuitry is part of the general electronics unit circuitry 23. In such arrangement, the coupling structure 15 is provided between the adhesive pad 13 and the electronics unit 2. In such embodiments, the electrodes 100a, 100b, 100c directly couple to the electronics unit 12 via corresponding releasable contacts, without further circuitry in-between.

In a further embodiment, the functionality of the electronics unit 2, in particular the electronics communication unit 22, memory 21, and the general electronics circuitry is integral with the disposable electronics unit 11 in a common housing and permanently attached to the adhesive pad 13, with the sensor 10, the adhesive pad 13, and the disposable electronics unit 11 favourably forming a common and undetachable unit and in particular a unit with direct galvanic coupling between electrodes 100a, 100b, 100c and the associated measurement circuitry.

The control device 3 is exemplarily realized as mobile general purpose device, in particular a smartphone as generally known, or a similar device, such as a tablet computer, running a dedicated application respectively software code. Alternatively, the control device may be a dedicated special-purpose device.

The control device 3 includes a reading device 31, a local control device communication unit 30, a memory 32, a remote control device communication unit 33, and general control device circuitry 34.

The general control device circuitry 34 includes a user interface with input/output functionality, e. g. a touch screen, power supply, power management circuitry, and the like. Typically, the control device 3 includes one or more microcomputers and/or microcontrollers which execute corresponding firmware and/or software code. The control device 3 serves for controlling operation of the analyte measurement system and in particular for showing measured analyte data, e. g. glucose data, typically in form of diagrams, symbols, numbers, etc. The control device 3 typically further serves for entering calibration data that are transmitted to the patch device and may include supplementary functionality such as analyte concentration statistics, trend analysis, alerting in case of undesirable high or low analyte concentration values, e. g. glucose concentration values, etc.

The reading device 31 is exemplary a camera as generally present in a smartphone. It may also be another type of reading device provided that it is suited to read the information of the sensor identifier 121. The local control device communication unit 30 is designed or suited for establishing a local communication link via communication with the electronics communication unit 22, exemplarily via Bluetooth.

The remote control device communication unit 33 is designed for establishing a communication link with further devices and include, e. g. a WLAN unit and/or 3G unit, for establishing a communication link an e. g. via the internet and/or available cellular device communication infrastructure. The remote control device communication unit 33 is especially designed for establishing a database communication link with the remote database 4.

Figure 2:
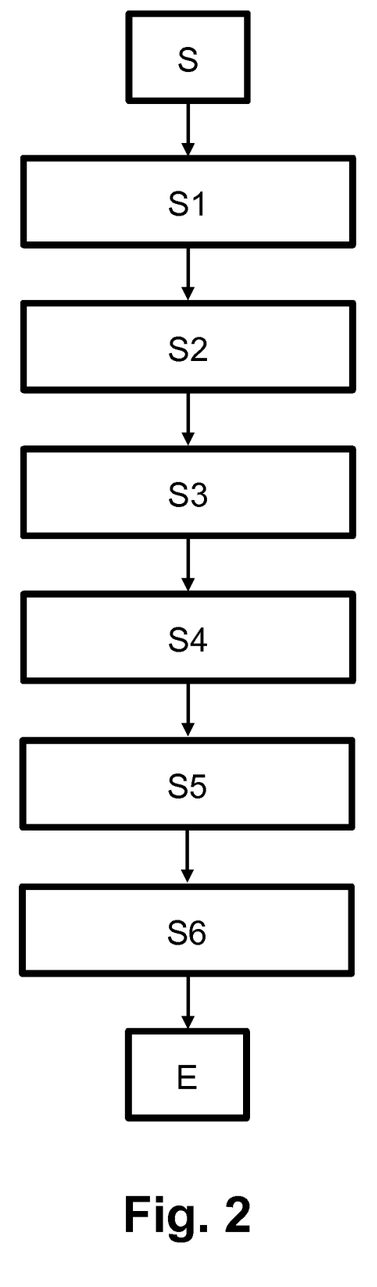
FIG. 2 shows major steps of an exemplary embodiment of a method for initializing an analyte measurement system.

In the following, reference is additionally made to FIG. 2. FIG. 2 shows major steps of an exemplary embodiment of a procedure or method for initializing an analyte measurement system, e. g. an analyte measurement system as shown in FIG. 1 and discussed before. After starting the procedure (S), a user of the analyte measurement system reads, subsequent to removing a fresh disposable unit 1 from its sterile package, the sensor identifier as stored on Data Matrix 121 from this disposable unit 1, into the control device 3, using the reading device 31 (step S1). This step is carried out in substantially the same way as widely known for reading a bar code, Data Matrix etc. into a smartphone. The sensor identifier includes or is a batch identifier.

Subsequently, the sensor identifier is, via the remote control device communication unit 33, transmitted to the remote database 4 (step S2). The remote database 4 is implemented on corresponding computing infrastructure, e. g. on a corresponding server, but may also be a decentralized cloud-based database. The remote database 4 includes a communication unit for exchanging data with the remote control device communication unit 33 in particular using an internet-and/or web based communication link, typically including a WLAN and/or cellular device communication infrastructure.

Subsequently, the remote database 4 determines, based on the received sensor identifier of the disposable unit 1, the matching initialization data set, i. e. the initialization data set that corresponds to the sensor identifier (step S3). A number initialization data sets is prestored by the remote database together with correspondence information between sensor identifiers and initialization data sets. Typically, whenever new a new batch of disposables are brought to sale, a corresponding initialization data set is stored in the remote database 4.

Subsequently, matching initialization data are transmitted from the remote database 4 to the control device 3 (step S4) and, via the local control device communication unit 30 and the electronics communication unit 22, form the control device 3 to the electronics unit 2 (step S5).

Subsequently, the initialization data are stored in the memory 21 of the electronics unit 2 for the following application time of the disposable unit 1 (step S6) and the procedure ends (E). Subsequently, the properly initialized system may be used. The initialization data may directly be or include calibration information that is applied, during the application time of the disposable unit 1, for calibration purposes. The calibration data may include parameters such as sensitivities, slopes, offsets, linearization parameters etc. Alternatively or additionally, calibration information may be computed from the received initialization data. In such embodiments, the initialization data are stored in the memory 21 not directly but in a processed form. Such processing, i. e. computing the calibration information from the initialization data, may be carried out by the control device 3 prior to the transmission to the electronics unit 11 in step S5), or directly by the electronics unit 11 in step S6.

Exemplarily, the initialization data further include expiry data of the disposable unit 1. This expiry data may be evaluated by the control device 3 and/or the electronics unit 11. The control device 3 and/or the electronics unit 2 may be configured to check the expiry data before starting use, or before even transmitting the initialization data from the control device 3 to the electronics unit 2. The control device 3 may be configured to provide a warning if the expiry date has passed or lies within the application time period of the disposable unit 1. In a variant, application and usage of the disposable unit 1 is prevented.

In a further variant, the expiry data is checked, based on the received sensor identifier, by the remote data base 4, e. g. as part of step S3 or step S4, and the initialization data are only transmitted to the control device (step S4) if the expiry date is not overdue.

In a further variant, the remote database 4 is configured to store, for each batch or even sub-batch of disposables, validity information. The validity information indicates whether a batch or sub-batch of disposable units is fine for use. In case, e. g. a manufacture problem or the like is identified for individual batches or sub-batches, the corresponding validity information may be changed, indicating that a disposable of the affected batch or sub-batch should not be used. In case a sensor identifier belonging to an affected batch or sub-batch is received by the remote database (step S2), a corresponding warning or error message may be transmitted to the control device 3 in step S4 rather than or additionally to the initialization data.

In a favorable embodiment, the favorably unique sensor identifier is transmitted from the control device 3 to the electronics unit 2 in step S5 and stored in the memory 21 in step S6. In this way, the sensor identifier is available in the memory 21 after the inserter device 12 is discarded, which is favorably in the context of complaints, as explained further below.

The procedure as shown in FIG. 2 is repeated every time the disposable unit 1 is replaced.

Figure 3:
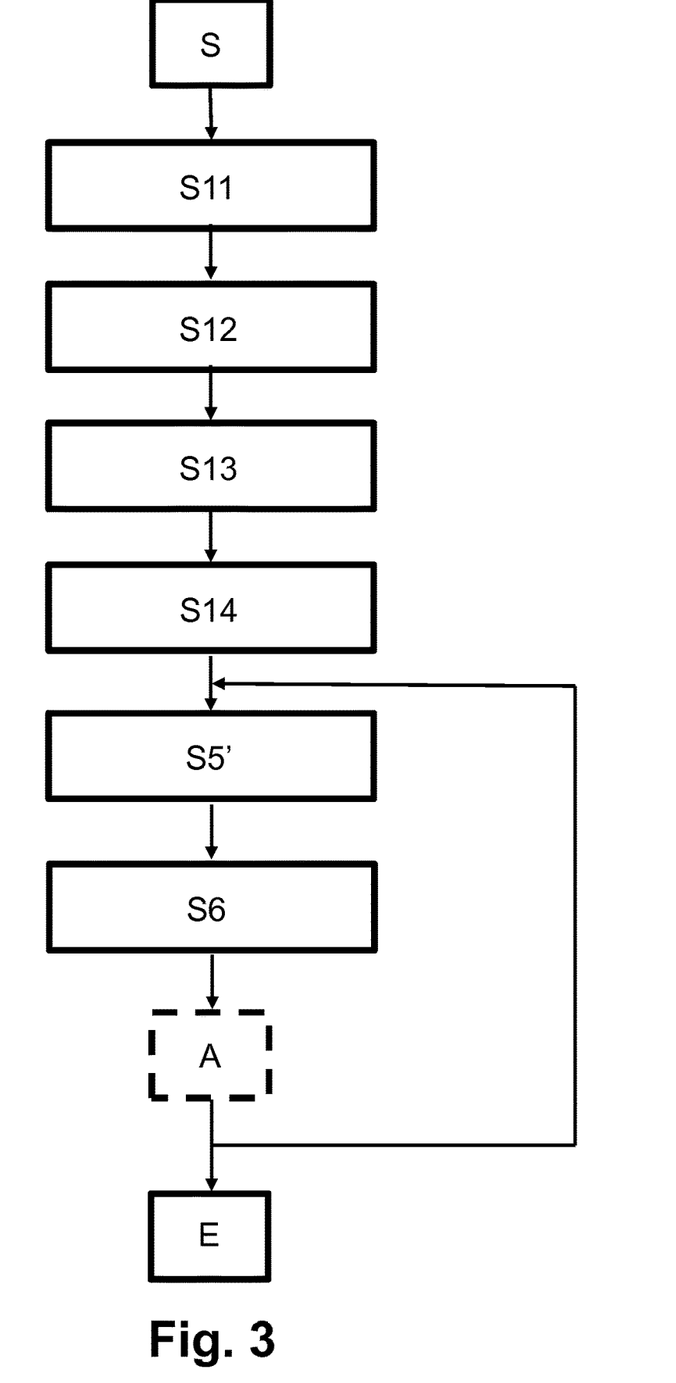
FIG. 3 shows major steps of a further exemplary embodiment of a method for initializing an analyte measurement system.

In the following, reference is additionally made to FIG. 3. FIG. 3 shows major steps of a further exemplary embodiment in accordance with the present disclosure. For the sake of conciseness, the description focusses on differences to the before-discussed embodiment, including its variants.

Steps S11, S12, S13 S14 correspond, in principle, to steps S1, S2, S3, S4, as explained before. In the embodiment of FIG. 3, however, each of these steps are carried out for a number of disposable units 1. The number of disposable units 1 typically belongs to a package of disposable units 1 that are purchased by a user, e. g. a Person with Diabetes, together. In step S11, the individual sensor identifiers of all the disposable units 1 are read into the control device 3 in sequence and are transmitted from the control device 3 to the remote database 4 in common in step S12. In step 13, a matching initialization data set is determined by the remote database 4 for each of received sensor identifiers. In step S14, all the matching initialization data sets are transmitted form the remote database 4 to the control device 3 and stored by the control device 3 in the memory 32 of the control device 3.

The subsequent step S5' largely corresponds to step S5 as explained before with reference to FIG. 2. Step S6 is carried out in the same way as explained before with reference to FIG. 2. The following differences, however, are present:

After storing the matching initialization data for a specific disposable 1 in the electronics unit 2 (step S6), the electronics unit 2 is used together with this specific disposable unit 1 in a subsequent application step (step A) for an application time period as explained before. The application step A belongs, as such, generally not to the initialization method and includes using the analyte measurement system for analyte measurement as explained before. At the end of the application time period, the steps S5', S6, A, are repeated for another disposable unit 1 from the number of disposable units 1. Since the matching initialization data for all of the disposable units are store and available in the control device 3, no e. g. internet and/or web-based link to the remote database 4 is required, but only less critical communication between the electronics unit 2 and the control device 3.

Only after all disposable units from the number of disposable units have been used, the overall procedure of FIG. 3 is repeated for a new number of disposable units, e. g. a new package.

In the method according to FIG. 3, it must be ensured that the initialization data that are transmitted to the electronics unit 1 actually fit the specific disposable unit 1 that shall be used next. Therefore, step S5' incudes, prior to transmitting initialization data from the control device 3 to the electronics unit 1 1, reading the sensor identifier from the specific disposable unit 1 that shall be used next into the control device 3 and determining the specific matching initialization data set from the stored initialization data sets. This specific initialization data set is then transmitted to the specific disposable unit 1 that shall be used next.

The steps that are associated with retrieving initialization data from the remote database 4, in particular a sequence of steps S1, S2, S3, S4, in the embodiment of FIG. 2 or a sequence of steps S11, S12, S13, S14 in the embodiment of FIG. 3, may in principle be carried out at any desired time, independent from the further steps, and also while another disposable unit is in used. The steps S1, S2, S3, S4, respectively S1, S12, S13, S14 may, in combination form a "Retrieve Initialization Data" routine that may be initiated by a user via the user interface of the control device 3. The sequence of steps S5, S6, respectively, S5', S6 may be or may be part of a "Set Sensor" or "Replace Sensor" routine that may be initiated by the user each time the disposable unit 1 is changed respectively replaced.

As mentioned before, a unique identifier, e. g. a unique serial number of the disposable unit 1, is transmitted to the electronics unit 2 in step S5 respectively step S5' and stored in the memory 21.

In case of a complaint, e. g. a potential malfunctions of a disposable unit 1, the electronics unit 2 may be returned e. g. to the manufacturer. The manufacturer can accordingly specifically identify the disposable unit 1 without physical presence of the disposable unit 1, which is difficult as explained before. At the manufacturer or more generally a service facility, the sensor identifier may accordingly be read out via the electronics communication unit 22 by an analysis device that is part of or coupled to a production management system and a matching may be carried out with production data from a production database.

The invention claimed is:

1. An analyte measurement system, the measurement system being designed for continuous in-vivo measurement of a body fluid analyte concentration, the analyte measurement system comprising:
   a skin-mountable patch device;
   a separate control device; and a plurality of disposable units, each disposable unit including a transcutaneous analyte sensor and a machine-readable sensor identifier unique for the analyte sensor, each of the disposable units having a matching initialization data set including sensor calibration information;

the patch device including one disposable unit of the plurality of disposable units, and further including an electronics unit configured to operate with each of the plurality of disposable units, the electronics unit being configured to releasably couple for an application time period to the one disposable unit, the electronics unit being configured to receive from the control device the matching initialization data set for the one disposable unit and to store the received matching initialization data set in a memory of the electronics unit, the control device including a reading device, the control device being configured:

to read into the control device in sequence, via the reading device, the sensor identifier from each of the plurality of disposable units and to transmit the sensor identifiers in common to a remote database via a database communication link;

to receive the matching initialization data set for each of the sensor identifiers from the remote database via the database communication link;

to read into the control device a second time, via the reading device, the sensor identifier for the one disposable unit of the plurality of disposable units;

to determine for the one disposable unit the specific matching initialization data set from the matching initialization data sets, the specific matching initialization data set matching the sensor identifier of the one disposable unit; and to transmit the specific matching initialization data set to the electronics unit via a local communication link.

2. The analyte measurement system according to claim 1, wherein the database communication link includes at least one of a WLAN communication link and a general purpose mobile device communication link.

3. The analyte measurement system according to claim 1, wherein the analyte is glucose.

4. A method for initializing an analyte measurement system, the measurement system being designed for continuous in-vivo measurement of a body fluid analyte concentration, the method comprising:

providing an analyte measurement system according to claim 1;

reading into the control device, in sequence, via the reading device, the sensor identifier from each of the plurality of disposable units;

transmitting the sensor identifiers in common from the control device to a remote database via a database communication link;

receiving in the control device the matching initialization data set for each of the sensor identifiers from the remote database via the database communication link;

reading into the control device a second time, via the reading device, the sensor identifier for the one disposable unit of the plurality of disposable units;

determining for the one disposable unit the specific matching initialization data set from the matching initialization data sets, the specific matching initialization data set matching the sensor identifier of the one disposable unit; and transmitting the specific matching initialization data set from the control device to the electronics unit via a local communication link.

5. The method according to claim 4, the method including using the matching initialization data for calibrating the analyte sensor.

6. The method according to claim 4, wherein the initialization data sets each further include at least one of a batch identifier and a sensor expiry date.

7. The method according to claim 4, wherein the sensor identifier is provided on a package of the disposable unit and/or on an insertion device in releasable mechanical coupling with the analyte sensor.

8. The method according to claim 4, wherein the sensor identifier is provided as optically readable code and wherein the reading device is an optical reading device.

9. The method according to claim 4, the method including: transmitting the sensor identifiers to the remote database transmitting the matching initialization data set from the remote database to the control device via a web-based database communication link.

10. The method according to claim 4, further comprising, after transmitting the sensor identifiers to the remote database, altering sensor status information in the remote database, the sensor status information corresponding to the sensor identifier of each of the disposable units.

11. The method according to claim 4, and further comprising: transmitting the sensor identifier to the electronics unit and storing the sensor identifier in the memory of the electronics unit.

12. A method for providing complaint analysis data for an analyte sensor of an analyte measurement system, the analyte measurement system being designed for continuous in-vivo measurement of a body fluid analyte concentration, the method comprising:

carrying out the method for initializing the analyte measurement system according to claim 11;

transmitting the sensor identifier from the memory to an analysis device; and determining matching production related data by matching the sensor identifier with a plurality of production related data sets that are stored in a production system data base, the matching production related data matching the sensor identifier.

* * * * *